(12) United States Patent
Lei

(10) Patent No.: US 9,506,874 B2
(45) Date of Patent: Nov. 29, 2016

(54) INFRARED-BASED METROLOGY FOR DETECTION OF STRESS AND DEFECTS AROUND THROUGH SILICON VIAS

(71) Applicant: GLOBALFOUNDRIES Inc., Grand Cayman (KY)

(72) Inventor: Ming Lei, Malta, NY (US)

(73) Assignee: GLOBALFOUNDRIES INC., Grand Cayman (KY)

( * ) Notice: Subject to any disclaimer, the term of this patent is extended or adjusted under 35 U.S.C. 154(b) by 0 days.

(21) Appl. No.: 14/691,392

(22) Filed: Apr. 20, 2015

(65) Prior Publication Data

US 2015/0226681 A1    Aug. 13, 2015

Related U.S. Application Data

(62) Division of application No. 13/769,494, filed on Feb. 18, 2013, now Pat. No. 9,041,919.

(51) Int. Cl.
| | |
|---|---|
| *G01J 3/00* | (2006.01) |
| *G01N 21/95* | (2006.01) |
| *G01N 21/88* | (2006.01) |
| *G01N 21/956* | (2006.01) |
| *G01B 11/16* | (2006.01) |

(52) U.S. Cl.
CPC ......... *G01N 21/9505* (2013.01); *G01B 11/161* (2013.01); *G01N 21/8806* (2013.01); *G01N 21/95692* (2013.01); *G01N 2201/061* (2013.01); *G01N 2201/0668* (2013.01); *G01N 2201/12* (2013.01)

(58) Field of Classification Search
USPC .......................................................... 356/51
See application file for complete search history.

(56) References Cited

U.S. PATENT DOCUMENTS

| | | | |
|---|---|---|---|
| 6,587,282 B1 | 7/2003 | Wang et al. | |
| 6,709,875 B2 | 3/2004 | Gilbert et al. | |
| 6,879,449 B2 | 4/2005 | Wang et al. | |
| 7,369,235 B1 | 5/2008 | Janik et al. | |

*Primary Examiner* — Tri T Ton
(74) *Attorney, Agent, or Firm* — Williams Morgan, P.C.

(57) ABSTRACT

An approach for IR-based metrology for detecting stress and/or defects around TSVs of semiconductor devices is provided. Specifically, in a typical embodiment, a beam of IR light will be emitted from an IR light source through the material around the TSV. Once the beam of IR light has passed through the material around the TSV, the beam will be analyzed using one or more algorithms to determine information about TSV stress and/or defects such as imbedded cracking, etc. In one embodiment, the beam of IR light may be split into a first portion and a second portion. The first portion will be passed through the material around the TSV while the second portion is routed around the TSV. After the first portion has passed through the material around the TSV, the two portions may then be recombined, and the resulting beam may be analyzed as indicated above.

20 Claims, 3 Drawing Sheets

INFRARED-BASED METROLOGY FOR DETECTION OF STRESS AND DEFECTS AROUND THROUGH SILICON VIAS

CROSS-REFERENCE TO RELATED APPLICATIONS

This application is a divisional of co-pending application Ser. No. 13/769,494 filed Feb. 18, 2013.

BACKGROUND OF THE INVENTION

1. Technical Field

Embodiments of the present invention relate generally to infrared (IR)-based metrology. Specifically, embodiments of the present invention relate to the use of infrared (IR)-based metrology for the detection of stress and effects around through silicon vias (TSVs).

2. Related Art

Thermal-mechanical reliability has become a big concern for the implementation of through silicon vias (TSVs), which are a vital part of 3D integration designs. Specifically, the process-induced stresses due to CTE mismatch between silicon (Si) and copper (Cu) can cause detrimental effects on both the performance and reliability. Such effects include, among other, mobility degradation, Si cracking, device de-bonding, and TSV pop-out.

As such, the measurement and handling of TSV stresses have become an important part of device design and integration. Unfortunately, existing approaches typically require cross-sectioning of the device such as during use of processes such as electron microscopy. That is, microscopy may be limited by either sample surface topography or the requirement of physical damage to the sample being tested.

SUMMARY OF THE INVENTION

In general, aspects of the present invention relate to an approach for IR-based metrology for detecting stress and defects around/adjacent TSVs of semiconductor devices. Specifically, in a typical embodiment, a beam of IR light will be emitted from an IR light source through the material around a TSV. Once the beam of IR light has passed through the material around the TSV, the beam will be analyzed using one or more algorithms to determine information about TSV defects such as imbedded cracking, etc. In one embodiment, the beam of IR light may be split into a first portion and a second portion. The first portion will be passed through material around the TSV while the second portion is routed around the TSV. After the first portion has passed through the material around the TSV, the two portions may then be recombined, and the resulting beam may be analyzed as indicated above.

A first aspect of the present invention provides a method for infrared (IR)-based metrology, comprising: passing a beam of IR light from an IR light source through a material around a through silicon via (TSV) of a semiconductor device; and analyzing the beam of IR light after being passed through the material around a TSV to determine information pertaining to stress or defects around the TSV.

A second aspect of the present invention provides a method for infrared (IR)-based metrology, comprising: emitting a beam of IR light using an IR light source; passing the beam of IR light through a material around a through silicon via (TSV) of a semiconductor device along a predetermined path; and analyzing the beam after being passed through the material around a TSV to determine information pertaining to stress or defects around the TSV.

A third aspect of the present invention provides a method for infrared (IR)-based metrology, comprising: emitting a beam of IR light using an IR light source; splitting the beam of IR light into a first portion and a second portion; passing the first portion of the beam of IR light through a material around a through silicon via (TSV) of a semiconductor device; combining the first portion with the second portion after the passing; and analyzing the beam after the combining to determine information pertaining to stress or defects around the TSV.

BRIEF DESCRIPTION OF THE DRAWINGS

These and other features of this invention will be more readily understood from the following detailed description of the various aspects of the invention taken in conjunction with the accompanying drawings in which.

Figure 1:
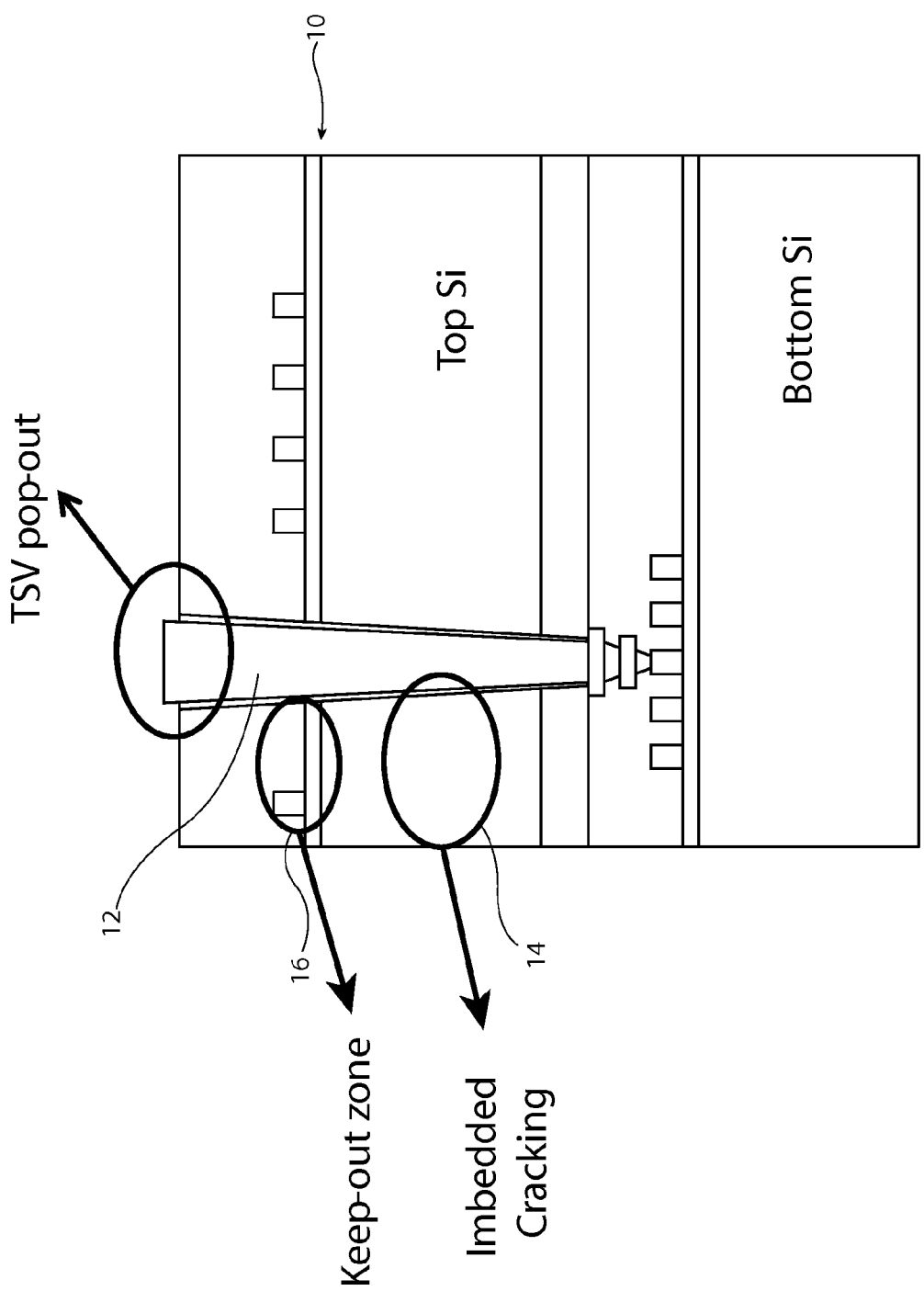
FIG. 1 shows an example of a semiconductor device having a through silicon via (TSV) device experiencing defects.

The drawings are not necessarily to scale. The drawings are merely representations, not intended to portray specific parameters of the invention. The drawings are intended to depict only typical embodiments of the invention, and therefore should not be considered as limiting in scope. In the drawings, like numbering represents like elements.

DETAILED DESCRIPTION OF THE INVENTION

Illustrative embodiments will now be described more fully herein with reference to the accompanying drawings, in which embodiments are shown. This disclosure may, however, be embodied in many different forms and should not be construed as limited to the embodiments set forth herein. Rather, these embodiments are provided so that this disclosure will be thorough and complete and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an", and "the" are intended to include the plural forms as well, unless the context clearly indicates otherwise. Furthermore, the use of the terms "a", "an", etc., do not denote a limitation of quantity, but rather denote the presence of at least one of the referenced items. The term "set" is intended to mean a quantity of at least one. It will be further understood that the terms "comprises" and/or "comprising", or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof.

Reference throughout this specification to "one embodiment," "an embodiment," "embodiments," "exemplary embodiments," or similar language means that a particular feature, structure, or characteristic described in connection with the embodiment is included in at least one embodiment of the present invention. Thus, appearances of the phrases "in one embodiment," "in an embodiment," "in embodiments" and similar language throughout this specification may, but do not necessarily, all refer to the same embodiment.

The terms "overlying" or "atop", "positioned on" or "positioned atop", "underlying", "beneath" or "below" mean that a first element, such as a first structure (e.g., a first layer) is present on a second element, such as a second structure (e.g. a second layer) wherein intervening elements, such as an interface structure (e.g. interface layer) may be present between the first element and the second element.

As indicated above, aspects of the present invention relate to an approach for IR-based metrology for detecting stress and defects around/adjacent TSVs of semiconductor devices. Specifically, in a typical embodiment, a beam of IR light will be emitted from an IR light source through material around a TSV. Once the beam of IR light has passed through the material around the TSV, the beam will be analyzed using one or more algorithms to determine information about TSV defects such as imbedded cracking, etc. In one embodiment, the beam of IR light may be split into a first portion and a second portion. The first portion will be passed through the material around the TSV while the second portion is routed around the TSV. After the first portion has passed through the material around the TSV, the two portions may then be recombined, and the resulting beam may be analyzed as indicated above.

Referring to FIG. 1, an example of a semiconductor device 10 having TSV 12 defects is shown. Specifically, as shown, TSV 12 has imbedded cracking inside material 14 as well as a "keep-out" zone 16. As indicated above such defects can greatly impact the design and/or integration of such devices. In previous approaches, to completely assess and address the defects, damage to the device was incurred due to necessary cross-sectioning thereof. However, the current approach obviates this requirement by utilizing an IR light-based metrology approach.

Figure 2:
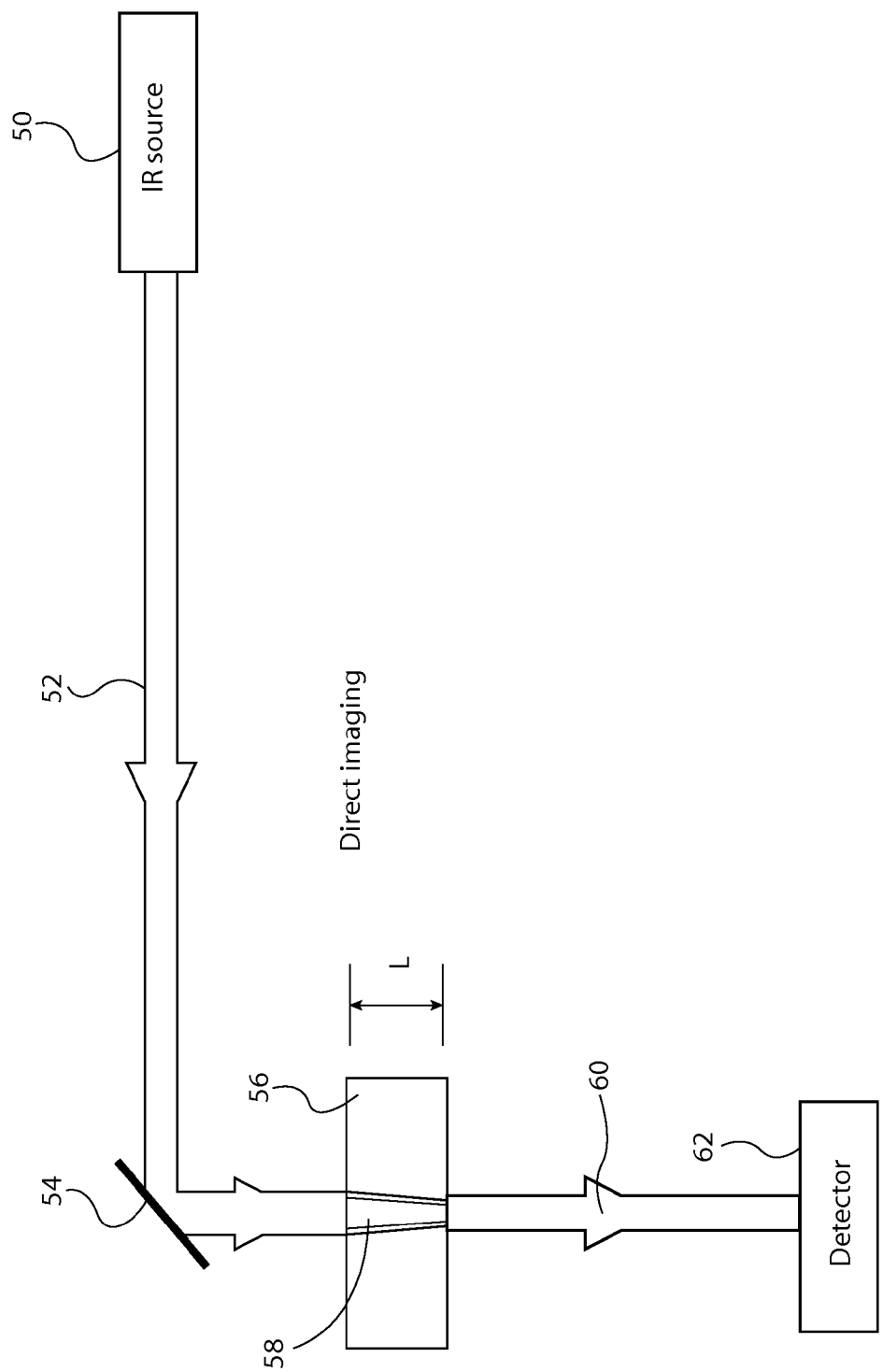
FIG. 2 shows the use of IR-based metrology for analyzing TSV defects according to an embodiment of the present invention.
Figure 3:
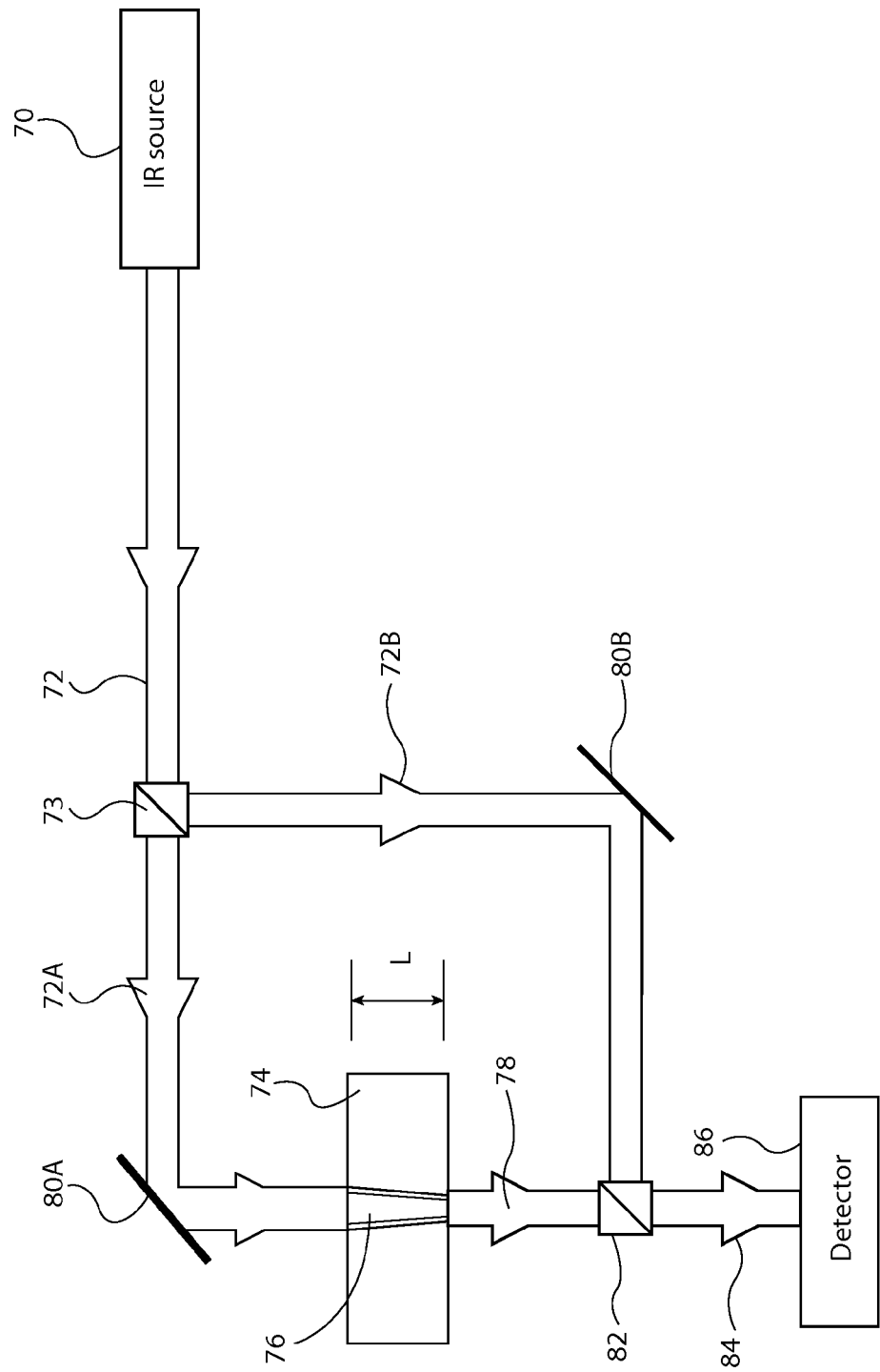
FIG. 3 shows the use of IR-based metrology for analyzing TSV defects according to another embodiment of the present invention.

Specifically, as will be shown and described in conjunction with FIGS. 2-3, the present approach passes a beam of IR light through the material around a TSV, and then analyzes the resulting beam. Is general, this approach utilizes an IR light beam with photon energy smaller than Si band gap (1.12 eV) that becomes transparent and can thus can provide in-depth information along the entire length of a TSV. In general, the following principles and algorithms will be applied hereunder. One such principle is that uniform "media" will generate well-defined periodic fringes. Such media can reveal various pieces of information about the TSV and/or its condition. According to the piezo-optic effect:

$$\Delta \epsilon_{ij}(\omega) = P_{ijkl}(\omega) X_{kl}$$

where $X_{kl}$ is the stress tensor and $P_{ijkl}$ is the piezo-optic tensor. Thus, the distribution of stress or buried cracking defects lead to a perturbation of index of refraction along the beam path (as well as a stress dependent phase shift), which may be revealed by the following algorithm:

$$\Delta \phi(x, y) = \int_0^T \Delta n(x, y, z) \frac{2\pi}{\lambda} z \, dz$$

where T is the total thickness of Si wafer. This results in distortion of fringes around the TSV, and the amount of distortion can be estimated as: $P \sim 10^{-9}$ $Pa^{-1}$, $X \sim 100$ Mpa, $T \sim 100$ m, so the phase shift is $\Delta\phi \sim 32$ rad, which is a very significant effect.

Referring to FIG. 2, a direct imaging approach according to one aspect of the present invention is shown. As depicted, an IR light source 50 emits a beam of IR light 52 (e.g., less than approximately 1.12 eV). One or more optics 54 may be used to direct beam 52 into TSV 58 of semiconductor device 56. Beam 52 will pass through the length of TSV 58. The resulting beam 60 will contain a perturbation of index of a refraction and other anomalies and may be received and analyzed by detector 62 to determine information pertaining to stress or defects around TSV 58.

Referring to FIG. 3, an interferometry-based approach is shown. As depicted, a beam of IR light 72 is emitted from IR light source 70 (e.g., less than approximately 1.12 eV). Beam 72 will be split by beam splitter 73 into first portion 72A and second portion 72B. As further shown, first portion 72A will be passed through TSV 76 of semiconductor device 74 (e.g., via optic(s) 80A) while portion 72B is routed around device 74. The resulting beam 78 will be recombined with portion 72B by beam combiner 82 (e.g., via optic(s) 80B) to yield a recombined beam 84 that will be analyzed by detector 86 similar to FIG. 2 to determine information about stress or defects in or around TSV 76. Using this approach may yield improved contrast and resolution and provide a basis for comparison (i.e., between portion 72A passing through the material around the TSV 76 and portion 72B).

As shown and described, the IR-based approaches discussed herein can provide a non-invasive, in-situ and high through-put detection of stress around a TSV pattern. These approaches can also be used as a real time monitor of stress during thermal cycling in order to prevent the formation of high stress and defects for process optimization. Moreover, the approaches can provide in-depth information regarding buried stress and/or defects around a TSV without cross sectioning the sample. The interferometry (phase sensitive) technique of FIG. 3 can provide much better contrast, resolution and sensitivity.

In various embodiments, design tools can be provided and configured to create the data sets used to pattern the semiconductor layers as described herein. For example, data sets can be created to generate photomasks used during lithography operations to pattern the layers for structures as described herein. Such design tools can include a collection of one or more modules and can also include hardware, software, or a combination thereof. Thus, for example, a tool can be a collection of one or more software modules, hardware modules, software/hardware modules, or any combination or permutation thereof. As another example, a tool can be a computing device or other appliance on which software runs or in which hardware is implemented. As used herein, a module might be implemented utilizing any form of hardware, software, or a combination thereof. For example, one or more processors, controllers, application-specific integrated circuits (ASIC), programmable logic arrays (PLA)s, logical components, software routines, or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

While the invention has been particularly shown and described in conjunction with exemplary embodiments, it will be appreciated that variations and modifications will occur to those skilled in the art. For example, although the illustrative embodiments are described herein as a series of acts or events, it will be appreciated that the present invention is not limited by the illustrated ordering of such acts or events unless specifically stated. Some acts may occur in different orders and/or concurrently with other acts or events apart from those illustrated and/or described herein, in accordance with the invention. In addition, not all illustrated steps may be required to implement a methodology in accordance with the present invention. Furthermore, the methods according to the present invention may be implemented in association with the formation and/or processing of structures illustrated and described herein as well as in association with other structures not illustrated. Therefore, it is to be understood that the appended claims are intended to cover all such modifications and changes that fall within the true spirit of the invention.

What is claimed is:

1. A method for infrared (IR)-based metrology, comprising:
    passing a beam of IR light from an IR light source through a material around a through silicon via (TSV) of a semiconductor device; and
    analyzing the beam of IR light after being passed through the material around the TSV to determine information pertaining to stress or defects around the TSV.

2. The method of claim 1, the analyzing comprising measuring a perturbation of a set of optical properties of the material around the TSV along a path of the beam of IR light.

3. The method of claim 2, the measuring comprising applying the following algorithm:

$$\Delta\phi(x, y) = \int_0^T \Delta n(x, y, z) \frac{2\pi}{\lambda} z\, dz,$$

wherein T is the total thickness of the semiconductor device, $\Delta n(x,y,z)$ is the index of refraction perturbation due to stress at a location $(x,y,z)$ in the semiconductor device, $\lambda$ is the wavelength of the beam, and $\Delta\Phi(x,y)$ is a phase perturbation on a plane $(x,y)$ of the semiconductor device.

4. The method of claim 1, further comprising:
    emitting a beam of IR light from the IR source; and
    splitting the beam into a first portion and a second portion, the passing comprising passing the first portion through the material around the TSV.

5. The method of claim 4, further comprising combining the first portion and the second portion after the first portion has passed through the material around the TSV.

6. The method of claim 5, the analyzing comprising analyzing the beam of IR light after the combining.

7. The method of claim 1, the beam of IR light having a photon energy less than approximately 1.12 eV.

8. A method for infrared (IR)-based metrology, comprising:
    emitting a beam of IR light using an IR light source;
    passing the beam of IR light through a material around a through silicon via (TSV) of a semiconductor device along a predetermined path; and
    analyzing the beam after being passed through the material around the TSV to determine information pertaining to stress or defects around the TSV.

9. The method of claim 8, the analyzing comprising measuring a perturbation of an index of refraction along a path of the beam.

10. The method of claim 9, the measuring comprising applying the following algorithm:

$$\Delta\phi(x, y) = \int_0^T \Delta n(x, y, z) \frac{2\pi}{\lambda} z\, dz,$$

wherein T is the total thickness of the semiconductor device, $\Delta n(x,y,z)$ is the index of refraction perturbation due to stress at a location $(x,y,z)$ in the semiconductor device, $\lambda$ is the wavelength of the beam, and $\Delta\Phi(x,y)$ is a phase perturbation on a plane $(x,y)$ of the semiconductor device.

11. The method of claim 8, further comprising splitting the beam of IR light into a first portion and a second portion, the passing comprising passing the first portion through the material around the TSV.

12. The method of claim 11, further comprising combining the first portion and the second portion after the first portion has passed through the material around the TSV to yield a recombined beam of IR light.

13. The method of claim 12, the analyzing comprising analyzing the recombined beam of IR light.

14. The method of claim 8, the beam of IR light having a photon energy less than approximately 1.12 eV.

15. The method of claim 4, further comprising routing the second portion of the beam of IR light around the material around the TSV.

16. The method of claim 1, the analyzing comprising applying an interferometry technique.

17. The method of claim 1, the method being performed in real-time.

18. The method of claim 11, further comprising routing the second portion of the beam of IR light around the material around the TSV.

19. The method of claim 8, the analyzing comprising applying an interferometry technique.

20. The method of claim 8, the method being performed in real-time.

* * * * *